US00PP27767P3

(12) United States Plant Patent
Egger

(10) Patent No.: US PP27,767 P3
(45) Date of Patent: Mar. 7, 2017

(54) ***HEUCHERA* PLANT NAMED 'RED LIGHTNING'**

(50) Latin Name: ***Heuchera* hybrid**
Varietal Denomination: Red Lightning

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 60 days.

(21) Appl. No.: 14/545,805

(22) Filed: Jun. 22, 2015

(65) Prior Publication Data

US 2016/0374252 P1 Dec. 22, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

New Plants and Flowers Jan. 13, 2015 *Heuchera* draws attention form across the garden, retrieved on Oct. 12, 2015, retrieved from the Internet at <http://www.newplantsandflowers.com/heuchera-draws-attention-from-across-the-garden/> 2 pp.*

* cited by examiner

*Primary Examiner* — June Hwu
(74) *Attorney, Agent, or Firm* — Klarquist Sparkman, LLP; Sheree Lynn Rybak

(57) ABSTRACT

A new and distinct *Heuchera* plant characterized by leaves which are yellow to lime green with prominent red veins, showing the strongest coloration in the spring and fall, large leaves, creamy white flowers on short flowering stems, a medium-large, mounding habit, and good vigor.

2 Drawing Sheets

Botanical denomination: *Heuchera* hybrid.
Variety designation: 'Red Lightning'.

BACKGROUND OF THE INVENTION

The present invention relates to a new and distinct cultivar of *Heuchera* and given the cultivar name of 'Red Lightning'. *Heuchera* is in the family Saxifragaceae. *Heuchera* 'Red Lightning' originated as a controlled cross using *Heuchera* 'K265-1', a proprietary, unpatented, unnamed plant as the seed parent, and *Heuchera* 'K259-1', a proprietary, unpatented, unnamed plant as the pollen parent.

Compared to the seed parent, *Heuchera* 'K265-1', the new cultivar is more vigorous and has a better crown count and darker pattern along the main veins.

Compared to the pollen parent, *Heuchera* 'K259-1', the new cultivar has larger leaves, a darker pattern along the main veins, and no veil.

Compared to *Heuchera* 'Delta Dawn', U.S. Plant Pat. No. 23,545, the new cultivar has larger leaves and habit, and a pattern that stays along the veins, rather than forming a red to dark center.

Compared to *Heuchera* 'Electric Lime', U.S. Plant Pat. No. 21,872, the new cultivar has a habit with more crowns and shorter internodes. The new cultivar has much more prominent red vein coloration.

This new *Heuchera* is uniquely distinguished by:

1. leaves which are yellow to lime green with prominent red veins, showing the strongest coloration in the spring and fall,
2. large leaves, 3. creamy white flowers on short flowering stems,
4. a medium-large, mounding habit, and
5. good vigor.

This new cultivar has been reproduced only by asexual propagation (tip cuttings and tissue culture). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows six-month-old plants of *Heuchera* 'Red Lightning' growing in a one gallon container, growing outside in shade in early July in Canby, Oreg.

FIG. 2 shows the same plants at eight months old.

FIG. 3 shows the same plants in late October in flower.

FIG. 4 shows six-week-old plants in 4 inch pots growing in a cool greenhouse in late April in Canby, Oreg.

DETAILED PLANT DESCRIPTION

The following is a detailed description of the new *Heuchera* cultivar based on observations taken in late October of nine-month-old specimens growing in one gallon containers, grown outside in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 5$^{th}$ edition, 2007.

Plant:

*Form.*—Basal rosette, herbaceous perennial.

*Hardiness.*—USDA Zone 4 to 9.

*Size.*—20 cm tall from top of the foliage to the ground and 50 cm wide.

*Number of crowns.*—4.

*Habit.*—Mounding.

*Vigor.*—Excellent.

Leaf:

*Type.*—Simple.

*Arrangement.*—Rosette.

*Shape.*—Broadly ovate to orbicular.

*Number.*—About 90.

*Lobing/division.*—7 shallow lobes, the terminal the longest, shallow secondary lobes.

*Venation.*—Palmate, both sides Yellow 11C in early spring maturing to Yellow Green 145C.

*Margins.*—Broadly, shallowly crenate, slightly undulate.

*Apex.*—Mucronulate.

*Base.*—Cordate, overlapping.

*Blade size.*—Grows to 16 cm long and 17 cm wide.

*Surface texture.*—Glandular hairs on both sides.

*Petiole description.*—Grows to 15 cm long and 3.5 mm wide, glandular hairs, Yellow Green 145C.

*Leaf color.*—Spring topside, between Greyed Yellow 162A and Yellow 11A with red along veins Greyed Purple 187B and between veins Greyed Purple 183A, bottom side 162A with pattern 183C; summer and fall topside, Yellow 12B to Green 138A with color along veins Greyed Purple 187C to 187B, bottom side Yellow Green 145B to 147C with color along veins Greyed Purple 183D; topside late summer to fall, Green 138A with color along veins 187B, bottom side147C with color along veins 183D; winter topside Green 138A, bottom side 147C.

Inflorescence:

*Size.*—Grows to 8.5 cm wide and 24 cm long.

*Type.*—Semi-upright thyrse.

*Number of flowers per thyrse.*—About 240, flower density moderate.

*Number of thyrse.*—About 14.

*Peduncle.*—Grows to 27 cm long and 3 mm wide at base, Yellow Green 152C, glandular hairs.

*Pedicel.*—Grows to 2.5 mm long, with glandular hairs, Yellow Green 152C.

*Bloom period.*—Late summer to fall.

Flower bud:

*Size.*—2.5 mm wide and 4 mm long.

*Description.*—Glandular puberulent, ovoid, down facing.

*Color.*—Orange White 159C.

Flower:

*Type.*—Perfect.

*Shape.*—Campanulate.

*Attitude.*—Side to down-facing.

*Size.*—6 mm long and 5 mm wide.

*Corolla description.*—5 petals, curl back, 3 mm long and less than 1 mm wide, spatulate, margins entire, tip acute, glabrous on top and glandular-puberulent on bottom side, White NN155B on both sides.

*Calyx description.*—Campanulate, 3 mm long and 3.5 mm wide, with 5 lobes divided ½ way to the base, each 1.5 mm wide and 2 mm long, glandular-puberulent on outside and glabrous inside, tip obtuse, margin entire, White 155A on both sides

*Stamen description.*—5 in number, filaments 4.5 mm long, White NN155A, anthers 0.4 mm, Orange 26A, no pollen.

*Pistil description.*—1, 2-beaked, 4 mm long and 2 mm wide, ovary 2 mm long and 2 mm wide, Green Yellow 1D, style 2 mm long, White NN155A.

*Fragrance.*—None.

*Lastingness.*—Each thyrse blooms for about 3 weeks on the plant.

Fruit and seed: None seed, infertile.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

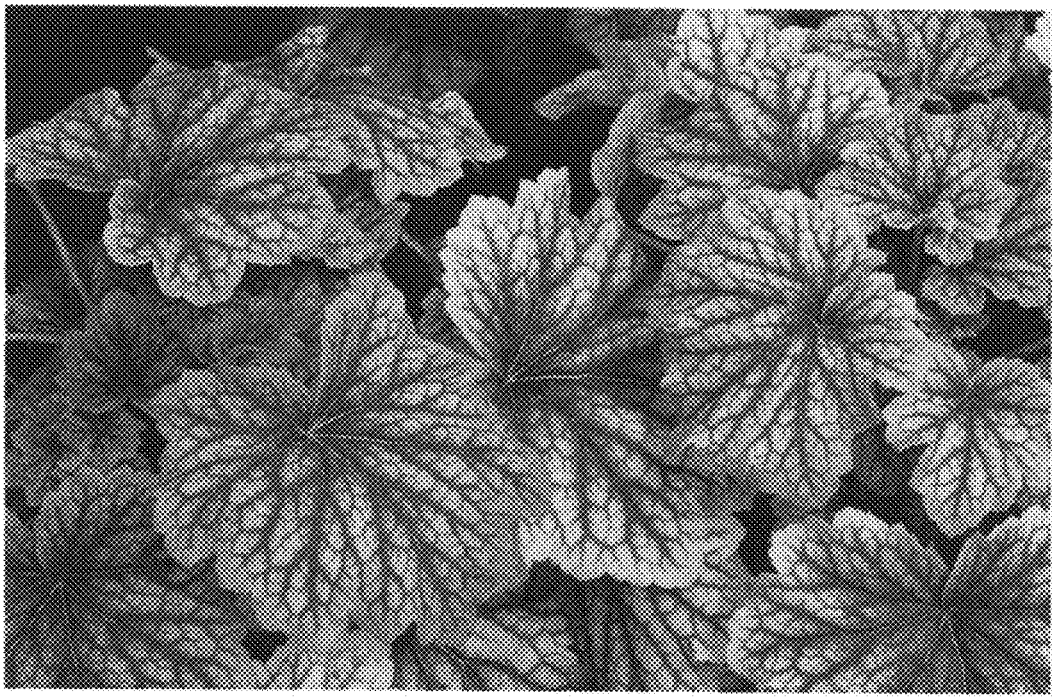
FIG.1 above, FIG. 2 below
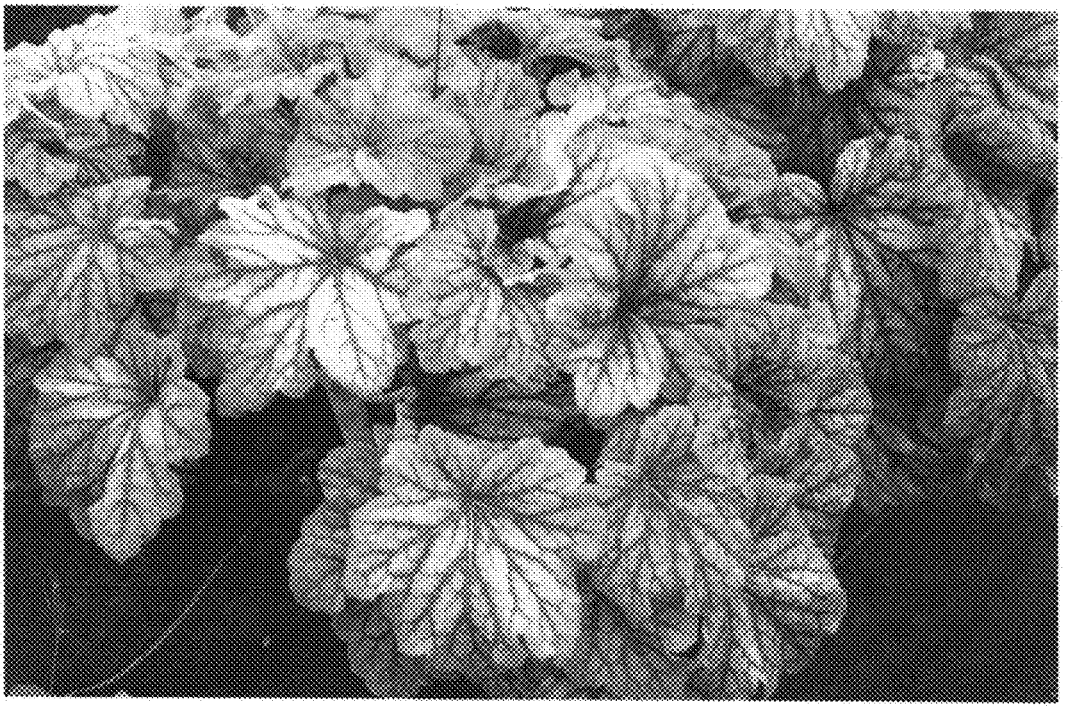

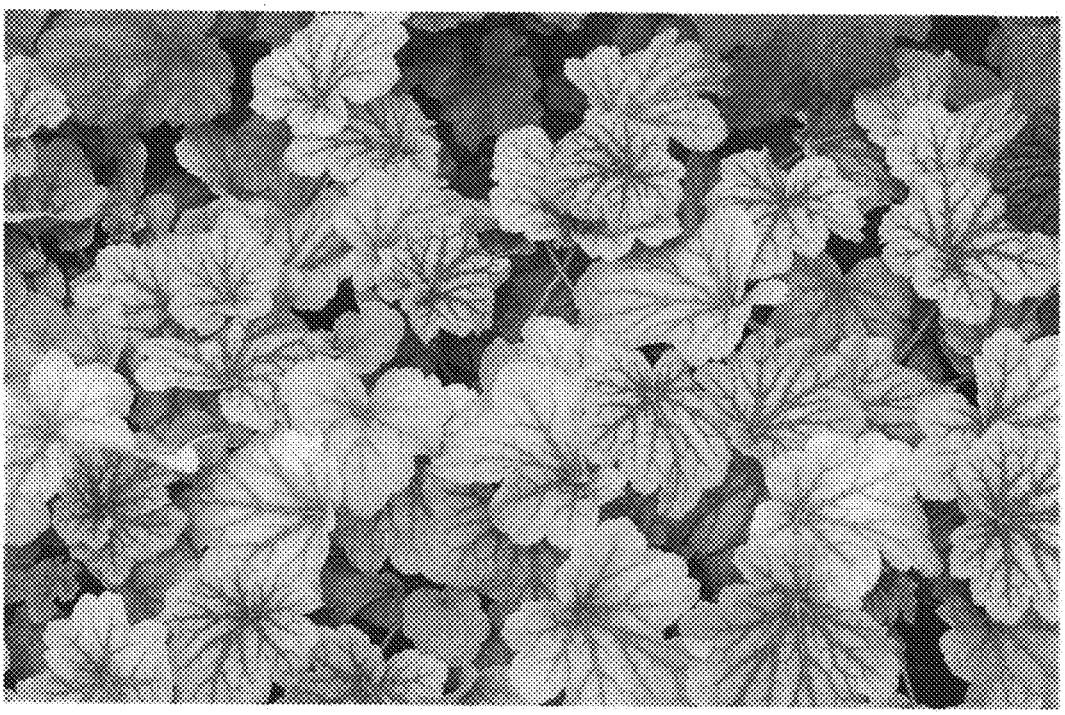

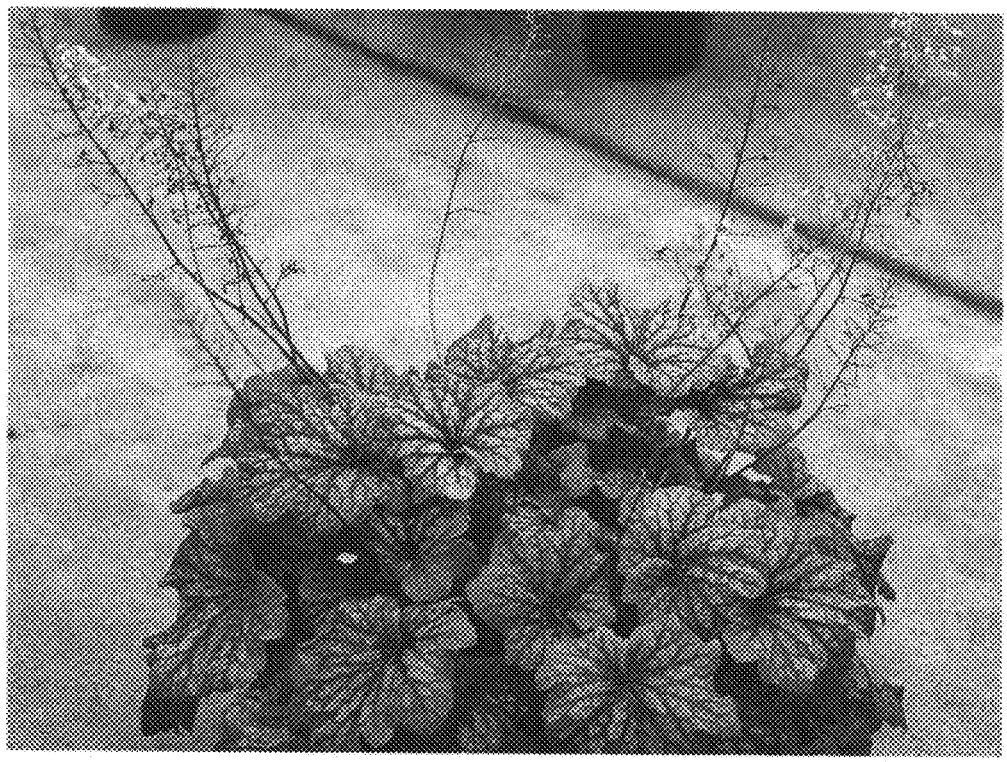
FIG. 3 above, FIG. 4 below